United States Patent [19]

Sada et al.

[11] Patent Number: 4,914,199

[45] Date of Patent: * Apr. 3, 1990

[54] PROCESS FOR PREPARING 4-ACETOXY-3-HYDROXYETHYLAZETIDIN-2-ONE DERIVATIVES

[75] Inventors: Isao Sada, Akashi; Kazunori Kan, Kobe; Noboru Ueyama, Kakogawa; Shingo Matsumoto, Takasago; Takehisa Ohashi, Kobe; Kiyoshi Watanabe, Akashi, all of Japan

[73] Assignee: Kanegafuchi Kagaku Kogyo Kabushiki Kaisha, Osaka, Japan

[ * ] Notice: The portion of the term of this patent subsequent to Apr. 3, 2007 has been disclaimed.

[21] Appl. No.: 156,873

[22] Filed: Feb. 18, 1988

[30] Foreign Application Priority Data

Feb. 20, 1987 [JP] Japan .................................. 62-38855
Feb. 25, 1987 [JP] Japan .................................. 62-42205
May 26, 1987 [JP] Japan .................................. 62-128630

[51] Int. Cl.$^4$ ........................ C07D 205/08; C07F 7/18; C07B 41/12
[52] U.S. Cl. ..................................................... 540/357
[58] Field of Search ......................................... 540/357

[56] References Cited
FOREIGN PATENT DOCUMENTS 167154 1/1986 European Pat. Off. ............ 540/357
247378 12/1987 European Pat. Off. ............ 540/357
62-84057 4/1987 Japan .................................. 540/357
62-195359 8/1987 Japan .................................. 540/357

*Primary Examiner*—Mark L. Berch
*Attorney, Agent, or Firm*—Armstrong, Nikaido, Marmelstein, Kubovcik & Murray

[57] ABSTRACT

A process for preparing a 4-acetoxy-3-hydroxyethylazetidin-2-one derivative having the formula (II):

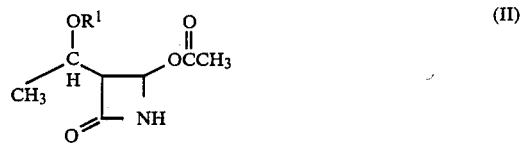

wherein $R^1$ is a protective group for the hydroxyl group, which comprises reactig a β-lactam compound having the formula (I):

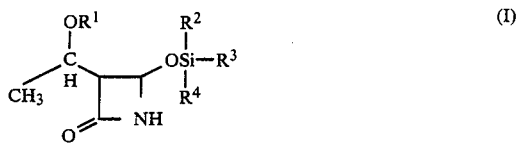

wherein $R^1$ is as difined above and $R^2$, $R^3$ and $R^4$ are the same or different and each is a lower alkyl group having 1 to 4 carbon atoms or an aralkyl group, with acetic anhydride in the presence of a base and a catalyst selected from the group consisting of an organic strong acid, a mineral acid, a Lewis acid, a halogenated acyl compound having the formula (IV):

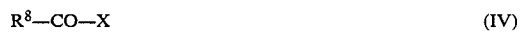

wherein $R^8$ is an alkyl group, an aralkyl group or phenyl group and X is a halogen atom, a halogenated sulfonyl compound having the formula (V):

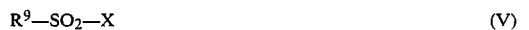

wherein $R^9$ is an alkyl group, an aralkyl group or phenyl group and X is a halogen atom, and a compound having the formula (VI):

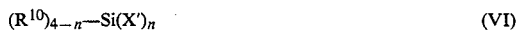

wherein $R^{10}$ is a lower alkyl group having 1 to 6 carbon atoms or phenyl group, X' is a halogen atom or $CF_3SO_2O$ group and n is an integer of 1 to 4. According to the present invention, there can be obtained 4-acetoxy-3-hydroxyethylazetidin-2-one derivatives, which are useful intermediates for preparing carbapenem β-lactam antibiotics, in high yield.

20 Claims, No Drawings

PROCESS FOR PREPARING 4-ACETOXY-3-HYDROXYETHYLAZETIDIN-2-ONE DERIVATIVES

BACKGROUND OF THE INVENTION

The present invention relates to a new process for preparing a 4-acetoxy-3-hydroxyethylazetidin-2-one derivative which has a hydroxyethyl group, wherein the hydroxyl group is protected, at the C3-position and has an acetoxyl group at the C4-position.

It is known that 4-acetoxy-3-hydroxyethylazetidin-2-one derivatives are useful intermediates for preparing carbapenem β-lactam antibiotics such as thienamycin and penem β-lactam antibiotics (cf., for example, Tetrahedron Letters by Reider et al., vol. 23, page 2293, 1982 and Chem. Pharm. Bull. by Yoshida et al., vol. 29, page 2899, 1981).

There hitherto have been known processes for synthesizing 4-acetoxy-3-hydroxyethylazetidin-2-one-derivatives, for instance, synthesis from 6-aminopenicillanic acid (cf. Chem. Pharm. Bull. by Yoshida et al., vol. 29, page 2899, 1981), synthesis from threonine (cf. Tetrahedron by Shiozaki et al., vol 39, page 2399, 1983) and synthesis from aspartic acid (cf. Tetrahedron Letters by Reider et al., vol. 23, page 2293, 1982). However, these processes have a problem that industrially unfavourable heavy metal compounds such as mercury acetate and lead tetraacetate are employed in order to introduce an acetoxyl group into the C4-position of the β-lactam ring.

The inventors found a process for introducing acetoxyl group into the C4-position of the β-lactam ring, at a low temperature, with using a β-lactam compound, wherein N is not protected, having an O-protected hydroxyethyl group at the C3-position and a silylether group at the C4-position (Japanese Unexamined Patent Publication No. 258353/1987).

SUMMARY OF THE INVENTION

It has now been found a process for introducing acetoxyl group into the C4-position of the β-lactam ring in a high yield at around room temperature by adding an acid, a halogenated acyl compound, a halogenated sulfonyl compound or a compound having the formula (VI):

$$(R^{10})_{4-n}-Si(X')_n \qquad (VI)$$

wherein $R^{10}$ is a lower alkyl group having 1 to 6 carbon atoms or phenyl group, $X'$ is a halogen atom or $CF_3SO_2O$ group and n is an integer of 1 to 4, to the reaction system in a catalytic amount.

According to the present invention, there is provided a process for preparing a 4-acetoxy-3-hydroxyethylazetidin-2-one derivative having the formula (II):

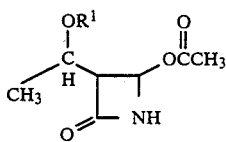

(II)

wherein $R^1$ is a protective group for the hydroxyl group, which comprises reacting a β-lactam compound having the formula (I):

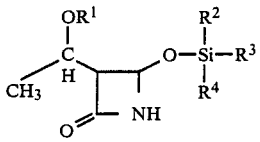

(I)

wherein $R^1$ is as defined above and $R^2$, $R^3$ and $R^4$ are the same or different and each is a lower alkyl group having 1 to 4 carbon atom or an aralkyl group, with acetic anhydride in the presence of a base and a catalyst selected from the group consisting of an organic strong acid, a mineral acid, a Lewis acid, a halogenated acyl compound having the formula (IV):

$$R^8-CO-X \qquad (IV)$$

wherein $R^8$ is an alkyl group, an aralkyl group or phenyl group and X is a halogen atom, a halogenated sulfonyl compound having the formula (V):

$$R^9-SO_2-X \qquad (V)$$

wherein $R^9$ is an alkyl group, an aralkyl group or phenyl group and X is a halogen atom, and a compound having the formula (VI):

$$(R^{10})_{4-n}-Si(X')_n \qquad (VI)$$

wherein $R^{10}$ is a lower alkyl group having 1 to 6 carbon atoms or phenyl group, $X'$ is a halogen atom or $CF_3SO_2O$ group and n is an integer of 1 to 4.

DETAILED DESCRIPTION

As shown in the patent application of the inventors (Japanese Unexamined Patent Publication No. 18791/1986), the β-lactam compound having the formula (I), which has a silylether group at the C4-position thereof, can be easily obtained by the process of the following reaction scheme I:

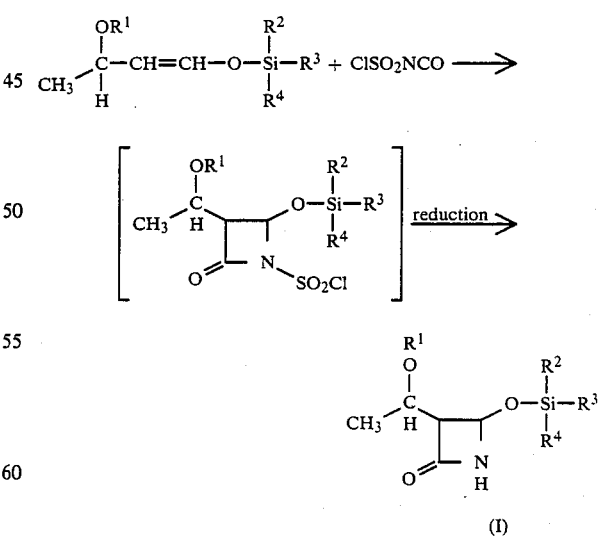

An example of the O-protective group of $R^1$ for the hydroxyethyl group at the C3-position i.e. the protective group for hydroxyl group, of the β-lactam compound (I) is, for instance, trialkylsilyl group having the formula (III):

wherein $R^5$, $R^6$ and $R^7$ are the same or different and each is a lower alkyl group having 1 to 6 carbon atoms provided that there is no case that all of the groups $R^5$, $R^6$ and $R^7$ have one carbon atom. Examples of such group (III) are, for instance, tert-butyldimethylsilyl group, triisopropylsilyl group, isopropyldimethylsilyl group, isobutyldimethylsilyl group, dimethyl-(1,2-dimethylpropyl)silyl group and dimethyl-(1,1,2-trimethylpropyl)silyl group. In addition, other examples of such group (III) are tert-butyl group, benzyl group, trichloroethoxycarbonyl group, tert-butoxycarbonyl group, p-nitrobenzyloxycarbonyl group, and the like. Among them, tert-butyldimethylsilyl group, isopropyldimethylsilyl group, dimethyl-(1,1,2-trimethylpropyl)silyl group and dimethyl-(1,2-dimethylpropyl)silyl group are preferable since they are stable during the reaction and can be selectively removed by acid treatment.

Groups $R^2$, $R^3$ and $R^4$ of the β-lactam compound having the formula (I) may be the same or different with each other, and selected from lower alkyl groups having 1 to 4 carbon atoms such as methyl, ethyl, isobutyl and 1,1,2-trimethylpropyl group and aralkyl groups such benzyl group, p-nitrobenzyl group. It is preferred all of $R^2$, $R^3$ and $R^4$ are the same and each is methyl group.

The β-lactam compound, prepared as mentioned above, having the formula (I):

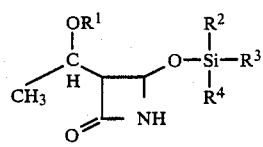

wherein $R^1$, $R^2$, $R^3$ and $R^4$ are as defined above, is reacted with acetic anhydride in the presence of a base to convert the β-lactam compound (I) into the desired 4-acetoxy-3-hydroxyethylazetidin-2-one derivative having the formula (II):

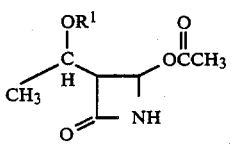

wherein $R^1$ is as defined above. In the above reaction, using an organic strong acid, a mineral acid, a Lewis acid, a halogenated acyl compound having the formula (IV):

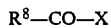

wherein $R^8$ and X are as defined above, a halogenated sulfonyl compound having the formula (V):

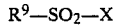

wherein $R^9$ and X are as defined above or a compound having the formula (VI):

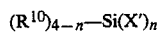

wherein $R^{10}$, X' and n are as defined above as a catalyst, remarkably increases the yield of the desired compound.

As for the organic strong acid, it is preferable to use, for instance, organic sulfonic acids such as p-toluenesulfonic acid, benzenesulfonic acid, xylenesulfonic acid, mesitylenesulfonic acid, trifluoromethanesulfonic acid, camphorsulfonic acid and pyridinesulfonic acid or organic proton acids having a strong acidity such as trifluoroacetic acid and trichloroacetic acid, and the like. Among them, an organic sulfonic acid, for instance, p-toluenesulfonic acid, and trifluoromethanesulfonic acid, and an organic proton acid, trifluoroacetic acid and trichloroacetic acid are more preferable to use.

As for the mineral acid, there may be used, for instance, hydrogen chloride, hydrogen bromide, hydrogen iodide, phosphoric acid, nitric acid, sulfuric acid and the like. The aqueous solutions thereof are also usable. Among them, hydrogen chloride and phosphoric acid are preferable to use.

As for the Lewis acid, it is preferable to use boron trifluoride and boron trichloride.

As for the halogenated acyl compound having the formula (IV), there may be used, for instance, acetyl chloride, acetyl bromide, acetyl iodide, trifluoroacetyl chloride, and the like. Among them, acetyl chloride is preferable to use.

As for the halogenated sulfonyl compound having the formula (V), there may be used, for instance, methanesulfonyl chloride, trifluoromethanesulfonyl chloride, toluenesulfonyl chloride, mesitylenesulfonyl chloride, and the like. Among them, p-toluenesulfonyl chloride is preferable to use.

As for the compound having the formula (VI), there may be used, for instance, trimethylsilyltrifluoromethanesulfonate, a trimethylhalosilane such as trimethylchlorosilane or trimethyliodosilane, a triethylhalosilane, a triisopropylhalosilane, a tripropylhalosilane, a triphenylhalosilane, a diphenylmethylhalosilane, a tert-butyldiphenylhalosilane, a tert-butyldimethylhalosilane, an isobutyldimethylhalosilane, an isopropyldimethylhalosilane, a dimethyl-(1,1,2-trimethylpropyl)halosilane, a dimethyl-(1,2-dimethylpropyl)halosilane, a tert-butylmethylphenylhalosilane, a dimethyldihalosilane, a diphenyldihalosilane, a methylpropyldihalosilane, a methyltrihalosilane, an ethyltrihalosilane, a propyltrihalosilane, a butyltrihalosilane, tetrachlorosilane, and the like. Among them, trimethylsilyltrifluoromethanesulfonate, trimethylchlorosilane and trimethyliodosilane are preferable to use.

In case the reaction of acetoxylation of the compound having the formula (I) is carried out only with acetic anhydride in the presence of a base but in the absence of the above-mentioned a catalyst, i.e. the organic strong acid, the mineral acid, the Lewis acid, the halogenated acyl compound having the formula (IV), the halogenated sulfonyl compound having the formula (V) and the compound having the formula (VI), most of the obtained products are the decomposed compounds wherein the β-lactam ring thereof is cleaved, and thereby the desired compound having the formula (II) cannot be obtained in a sufficient yield.

In the reaction of acetoxylation of the C4-position of the compound having the formula (I) in the presence of the above-mentioned catalyst, factors such as the amounts of catalyst, base and acetic anhydride, the kinds of solvent and base, and the reaction temperature affect the yield of the desired compound.

As for the base, it is preferably to use pyridines such as pyridine, picoline and rutidine. Among them, pyridine and picoline are more preferable to use.

As for the solvent, there may be used the above-mentioned base, or an organic solvent which does not react with the compound having the formula (I) and reagents such as the catalyst, the base and acetic anhydride. Examples of the solvent are methylene chloride, ethyl acetate, n-hexane, toluene, dimethylformamide, tetrahydrofuran. Among them, pyridines and dimethylformamide are preferred to used.

The above-mentioned catalyst may be used in an amount of 0.5 to 1 time mole to the β-lactam compound having the formula (I). Each of the base and acetic anhydride may be used in an amount of 1 to 30 times moles and 1 to 15 times moles respectively, to the β-lactam compound having the formula (I).

In case the reaction in the present invention is carried out in a solvent, reactants may be used in an usually used amount, for instance, from about 5 to about 30% by weight.

Preferably, the reaction is carried out at a temperature of −30° to 50° C.

The reaction is, for example, carried out by dissolving the β-lactam compound having the formula (I) having a silylether group at the C4-position, either in only a base such as pyridine or in a mixture of a solvent such as dimethylformamide and a base such as pyridine, followed by adding acetic anhydride and the catalyst i.e. the organic strong acids, the mineral acids, the Lewis acid, the halogenated acyl compound having the formula (IV), the halogenated sulfonyl compound having the formula (V) or the compound having the formula (VI), either at one time or at several times.

The reaction mixture is analyzed by means of thin layer chromatography during the reaction process, and added to water when the starting material, i.e. the β-lactam compound having the formula (I), in the reaction mixture disappears or almost disappears.

After extracting the reaction mixture with organic solvents such as n-hexane, the organic layer is washed with an aqueous solution of sodium hydrocarbonate and water, dried with magnesium sulfuric anhydride and then the organic solvent is distilled away to give crude crystals.

Finally, the desired 4-acetoxy-3-hydroxyethylazetidin-2-one derivative is obtained by subjecting the above crude crystals to recrystallization.

In case of using n-hexane as the extraction solvent, the 4-acetoxy-3-hydroxyethylazetidin-2-one derivative can be obtained as crystals by cooling the organic layer after drying the organic layer with anhydrous magnesium sulfate.

Another methods such as column chromatography may be employed to obtain the 4-acetoxy-3-hydroxyethylazetidin-2-one derivative from the resultant mixture, wherein the organic solvent has been distilled away.

The present invention is more particularly explained by the following non-limiting examples. However, it is to be understood that any modification or development can be made without departing from the scope and spirit of the present invention.

EXAMPLE 1

[Preparation of (3 R, 4 R)-4-acetoxy-3-[(R)-1-tert-butyldimethylsilyloxyethyl]azetidin-2-one]

There was dissolved 309 mg of (3 R, 4 R)-3-[(R)-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] in 1.55 ml of pyridine and the solution was cooled to 0° C., to which were added 0.51 ml of acetic anhydride and 56 mg of p-toluenesulfonic acid.H$_2$O, and the mixture was stirred at 0° C. for 36.5 hours. The reaction mixture was poured into 30 ml of water and extracted with 30 ml of n-hexane. After the organic layer was washed with 5% aqueous solution of NaHCO$_3$ and further saturated solution of salt, and dried with anhydrous magnesium sulfate, the resultant was filtered. Then, the solvent was distilled away under reduced pressure to give 288 mg of white solid.

The white solid was dissolved in n-hexane and insoluble substances were filtered off, then the resultant was allowed to stand while cooling at −15° C. to give 195 mg (yield: 69.7%) of needle-like crystal. The obtained crystal was found to be the desired (3 R, 4 R)-4-acetoxy-3-[(R)-1-tert-butyldimethylsilyloxyethyl]azetidin-2-one from the following values of the physical properties.

$[\alpha]_D^{25} = +50°$ (c=0.5, CHCl$_3$) mp: 107° C;

$^1$H NMR (90 MHz, CDCl$_3$) δ (ppm), 0.08 (6 H, s), 0.84 (9 H, s), 1.20 (3 H, d), 2.01 (3 H, s), 3.04 (1 H, dd), 4.12 (1 H, m), 5.76 (1 H, d), 6.73 (NH)

EXAMPLE 2

[Preparation of (3 R, 4 R)-4-acetoxy-3-[(R)-1-tert-butyldimethylsilyloxyethyl]azetidin-2-one]

There was dissolved 306 mg of (3 R, 4 R)-3-[(R)-1-tert-butyldimethylsilyloxyethyl]-4-trimethylsilyloxyazetidin-2-one [mp: 95° C. to 96° C., $[\alpha]_D^{25} = -9.5°$ (c=1.0, CHCl$_3$)] in 1.54 ml of pyridine and the solution was cooled to −5° C., to which were added 0.51 ml of acetic anhydride and 55 mg of p-toluenesulfonic acid.H$_2$O, and the mixture was stirred at −5° C. for 48 hours. The reaction mixture was poured into 30 ml of water and extracted with 30 ml of n-hexane. After the organic layer was washed with 5% aqueous solution of NaHCO$_3$ and further saturated solution of salt, and dried with anhydrous magnesium sulfate, the resultant was filtered. Then, the solvent was distilled away under reduced pressure to give 303 mg of white solid.

The white solid was analyzed by means of high performance liquid chromatography (column: YMC-packed column A-303 ODS, commercially available from Yamamura Chemical Company), 4.6×250 mm; column temperature: 15° C.; solvent: acetonitrile/water=6/4 (v/v); flow rate: 1.1 ml/min.; detection: 210 nm), and 217 mg (yield: 78%) of (3 R, 4 R)-4-acetoxy-3-[(R)-1-tert-butyldimethylsilyloxyethyl]-azetidin-2-one was found.

The results of specific rotation, melting point and NMR spectrum of the obtained compound were the same as those in Example 1.

EXAMPLE 3

[Preparation of (3 R, 4 R)-4-acetoxy-3-[(R)-1-tert-butyldimethylsilyloxyethyl]azetidin-2-one]

There was dissolved 301 mg of (3 R, 4 R)-3-[(R)-1-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] in 1.51 ml of pyridine and the solution was cooled to 9° C., to which were added 0.27 ml of acetic anhydride and 8 μl of trifluoromethanesulfonic acid, and the mixture was stirred at 9° C. for 38 hours. After completion of the reaction and the same treatment as in Example 2, the obtained white solid was analyzed by means of high performance liquid chromatography, and 179 mg (yield: 66%) of (3 R, 4 R)-4-acetoxy-3-[(R)-1-tert-butyldimethylsilyloxyethyl]azetidin-2-one was found.

The results of specific rotation, melting point and NMR spectrum of the obtained compound were same as those in Example 1.

EXAMPLE 4

[Preparation of (3 R, 4 R)-4-acetoxy-3-[(R)-1-tert-butyldimethylsilyloxyethyl]azetidin-2-one]

There was dissolved 301 mg of (3 R, 4 R)-3-[(R)-1-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] in 1.50 ml of pyridine, to which, at room temperature, were added 0.51 ml of acetic anhydride and 34 μl of a solution of 2.75N hydrogen chloride in dioxane, then the mixture was stirred for 23 hours at room temperature. After completion of the reaction and the same treatment as in Example 2, the obtained white solid was analyzed by means of high performance liquid chromatography, and 168 mg (yield: 62%) of (3 R, 4 R)-4-acetoxy-3-[(R)-1-tert-butyldimethylsilyloxyethyl]azetidin-2-one was found.

The results of specific rotation, melting point and NMR spectrum of the obtained compound were the same as those in Example 1.

EXAMPLE 5

[Preparation of (3 R, 4 R)-4-acetoxy-3-[(R)-1-tert-butyldimethylsilyloxyethyl]azetidin-2-one]

There was dissolved 300.8 mg of (3 R, 4 R)-3-[(R)-1-tert-butyldimethylsilyloxyethyl]-4-trimethylsilyoxyazetidin-2-one [mp: 95° to 96° C., $[\alpha]_D^{25} = -9.5°$ (C=1.0, CHCl$_3$)] in 1.53 ml of pyridine, to which were added 1.34 ml of acetic anhydride and 30.9 mg of trichloroacetic acid under nitrogen atmosphere, and the mixture was stirred at −5° C. for 40 hours. The reaction mixture was poured into 30 ml of water and extracted with 80 ml of n-hexane. After the organic layer was washed with 5% aqueous solution of NaHCO$_3$ and further saturated solution of salt, and dried with anhydrous magnesium sulfate, the resultant was filtered. Then, the solvent was distilled away under reduced pressure to give 274.1 mg of white solid. The obtained white solid was analyzed by means of high performance liquid chromatography, and 241.6 mg (yield: 89%) of (3 R, 4 R)-4-acetoxy-3-[(R)-1-tert-butyldimethylsilyloxyethyl]azetidin-2-one was found.

The results of specific rotation, melting point and NMR spectrum of the obtained compound were the same as those in Example 1.

EXAMPLE 6

[Preparation of (3 R, 4 R)-4-acetoxy-3-[(R)-1-tert-butyldimethylsilyloxyethyl]azetidin-2-one]

There was dissolved 301 mg of (3 R, 4 R)-3-[(R)-1-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] in 1.51 ml of pyridine, to which, at room temperature, were added 0.51 ml of acetic anhydride and 2 μl of phosphoric acid, and the mixture was stirred for 20 hours at room temperature. After completion of the reaction and the same treatment as in Example 2, the obtained white solid was analyzed by means of high performance liquid chromatography, and 158 mg (yield: 58%) of (3 R, 4 R)-4-acetoxy-3-[(R)-1-tert-butyldimethylsilyloxyethyl]azetidin-2-one was found.

The results of specific rotation, melting point and NMR spectrum of the obtained compound were the same as those in Example 1.

EXAMPLES 7 TO 12 AND COMPARATIVE EXAMPLE 1

[Preparation of (3 R, 4 R)-4-acetoxy-3-[(R)-1-tert-butyldimethylsilyloxyethyl]azetidin-2-one]

The procedure of Example 2 was repeated to prepare (3 R, 4 R)-4-acetoxy-3-[(R)-1-tert-butyldimethylsilyloxyethyl]azetidin-2-one [(II') shown below] except that various acids shown in Table 1 were employed as a catalyst and that acetic anhydride was used in an amount of 5.6 moles and pyridine was used in an amount of 19.7 moles to one mole of (3 R, 4 R)-3-[(R)-1-tert-butyldimethylsilyloxyethyl]-4-trimethylsilyloxyazetidin-2-one [(I') shown below]. Further, the reaction temperature and time employed were as shown in Table 1. Also, the same preparation as above was carried out without adding acids, for comparison. The results are shown in Table 1.

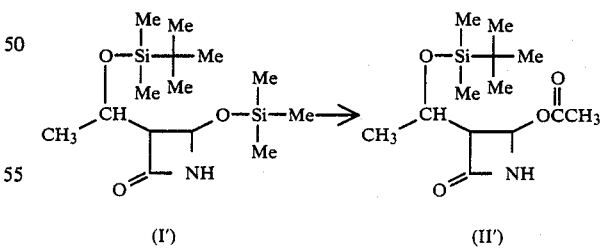

The results of specific rotation, melting point and NMR spectrum of the obtained compound in each Examples 7 to 12 were the same as those in Example 1.

TABLE 1

| Ex. No. | Acid | Amount of Acid (moles to one mole of the compound (I')) | Temperature | Time (hours) | Yield of the compound (II') (%) |
|---|---|---|---|---|---|
| 7 | D-Camphor-10-sulfonic acid | 0.1 | Room temperature | 18 | 65 |

TABLE 1-continued

| Ex. No. | Acid | Amount of Acid (moles to one mole of the compound (I')) | Temperature | Time (hours) | Yield of the compound (II') (%) |
|---|---|---|---|---|---|
| 8 | Trifluoroacetic acid | 0.1 | Room temperature | 18 | 59 |
| 9 | 3-pyridinesulfonic acid | 0.1 | Room temperature | 18 | 58 |
| 10 | Concentrated hydrochloric acid | 0.1 | Room temperature | 20 | 45 |
| 11 | $BCl_3$ | 0.1 | Room temperature | 21 | 47 |
| 12 | $BF_3.Et_2O$ | 0.18 | Room temperature | 39 | 24 |
| Com. Ex. 1 | — | 0 | Room temperature | 25 | 10 |

EXAMPLES 13 TO 15

[Preparation of (3 R, 4 R)-4-acetoxy-3-[(R)-1-tert-butyldimethylsilyloxyethyl]azetidin-2-one]

The procedure of Example 2 was repeated to prepare (3 R, 4 R)-4-acetoxy-3-[(R)-1-tert-butyldimethylsilyloxyethyl]azetidin-2-one [(II') shown below] except that acetyl chloride, p-toluenesulfonyl chloride or methanesulfonyl chloride shown in Table 1 was employed as a catalyst and that acetic anhydride was used in an amount of 8 moles and pyridine was used in an amount of 19.7 moles to one mole of (3 R, 4 R)-3-[(R)-1-tert-butyldimethylsilyloxyethyl]-4-trimethylsilyloxyazetidin-2-one [(I') shown below]. The reaction temperature and time employed were as shown in Table 2. The results are shown in Table 2.

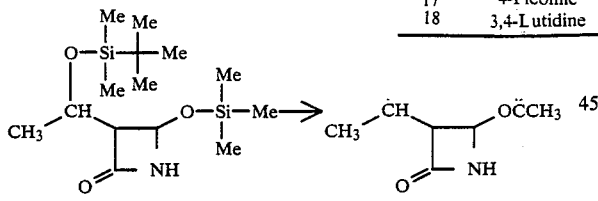

(I')     (II')

The results of specific rotation, melting point and NMR spectrum of the obtained compound in each Examples 13 to 15 were the same as those in Example 1.

TABLE 2

| Ex. No. | Halogenated acyl compounds | Amount of halogenated acyl compound (mole to one mole of the compound (I')) | Temperature (°C.) | Time (hours) | Yield of the compound (II') (%) |
|---|---|---|---|---|---|
| 13 | Acetyl chloride | 0.3 | 0 | 46 | 75 |
| 14 | p-Toluenesulfonyl chloride | 0.3 | 0 | 42 | 74 |
| 15 | Methanesulfonyl chloride | 0.3 | 0 | 42 | 61 |

EXAMPLES 16 TO 18

[Preparation of (3 R, 4 R)-4-acetoxy-3-[(R)-1-tert-butyldimethylsilyloxyethyl]azetidin-2-one]

The procedure of Example 2 was repeated to prepare (3 R, 4 R)-4-acetoxy-3-[(R)-1-tert-butyldimethylsilyloxyethyl]azetidin-2-one [(II') shown below] except that various bases shown in Table 3 were used and that acetic anhydride was used in an amount of 5.6 moles and p-toluenesulfonic acid.$H_2O$ was used in an amount of 0.2 mole to one mole of (3 R, 4 R)-3-[(R)-1-tert-butyldimethylsilyloxyethyl]-4-trimethylsilyloxyazetidin-2-one [(I') shown below]. The reaction temperature and time employed were as shown in Table 3. The results are shown in Table 3.

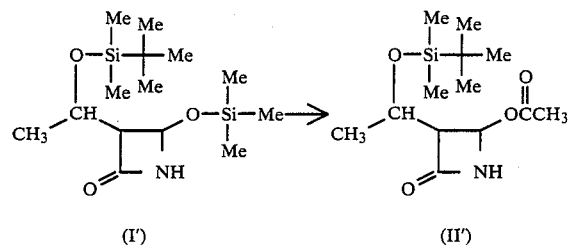

(I')     (II')

The results of specific rotation, melting point and NMR spectrum of the obtained compound in each Examples 16 to 18 were the same as those in Example 1.

TABLE 3

| Ex. No. | Base | Amount of base (moles to one mole of the compound (I')) | Temperature (°C.) | Time (hours) | Yield of the compound (II') (%) |
|---|---|---|---|---|---|
| 16 | 3-Picoline | 19.7 | 9 | 40 | 73 |
| 17 | 4-Picoline | 19.7 | 9 | 40 | 63 |
| 18 | 3,4-Lutidine | 19.7 | 9 | 46 | 59 |

EXAMPLES 19 TO 24

[Preparation of (3 R, 4 R)-4-acetoxy-3-[(R)-1-tert-butyldimethylsilyloxyethyl]azetidin-2-one]

The procedure of Example 2 was repeated to prepare (3 R, 4 R)-4-acetoxy-3-[(R)-1-tert-butyldimethylsilyloxyethyl]azetidin-2-one [(II') shown below] using (3 R, 4 R)-3-[(R)-1-tert-butyldimethylsilyloxyethyl]-4-trimethylsilyloxyazetidin-2-one [(I') shown below] as a starting material except that various solvent shown in Table 4 were used. Also, acetic anhydride, pyridine, p-toluenesulfonic acid, the reaction temperature and time were employed as shown in Table 1. The results are shown in Table 4.

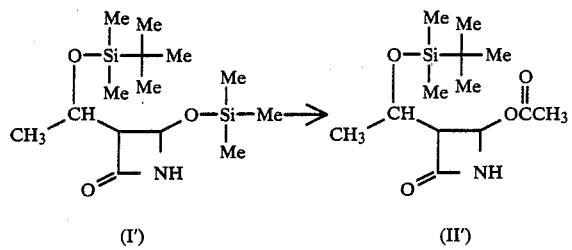

(I')      (II')

The results of specific rotation, melting point and NMR spectrum of the obtained compound in each Examples 19 to 24 were the same as those in Example 1.

TABLE 4

| Ex. No. | Compound (I') (mg) | Solvent (ml) | Acetic anhydride (ml) | Pyridine (ml) | p-Toluenesulfonic acid.H$_2$O (mg) | Temperature | Time (hours) | Yield of the compound (II') (%) |
|---|---|---|---|---|---|---|---|---|
| 19 | 301 | Dimethylformamide 0.74 | 0.50 | 0.77 | 36 | 9° C. | 53 | 67 |
| 20 | 299 | Tetrahydrofuran 1.17 | 0.50 | 0.43 | 18 | Room temperature | 17 | 38 |
| 21 | 320 | Ethyl acetate 1.14 | 0.53 | 0.46 | 19 | Room temperature | 18 | 35 |
| 22 | 308 | Toluene 1.16 | 0.51 | 0.43 | 18 | Room temperature | 17 | 35 |
| 23 | 311 | n-Hexane 1.16 | 0.52 | 0.44 | 19 | Room temperature | 18 | 32 |
| 24 | 297 | Methylene chloride 1.18 | 0.49 | 0.42 | 18 | Room temperature | 17 | 24 |

EXAMPLE 25

[Preparation of (3 R, 4 R)-4-acetoxy-3-[(R)-1-[dimethyl-(1,1,2-trimethylpropyl)silyloxy]ethyl]azetidin-2-one]

There was dissolved 321 mg of (3 R, 4 R)-3-[(R)-1-[dimethyl-(1,1,2-trimethylpropyl)silyloxy]ethyl]-4-trimethylsilyloxyazetidin-2-one in 1.51 ml of pyridine and the solution was cooled to 9° C., to which were added 0.50 ml of acetic anhydride and 36 mg of p-toluenesulfonic acid.H$_2$O, and the mixture was stirred at 9° C. for 40 hours. After completion of the reaction, the reaction mixture was treated in the same manner as in Example 2 to give 250 mg of semi-solid. The obtained semi-solid was treated by means of silica-gel column chromatography [n-hexane/ethyl acetate=10/1 (v/v)], and further recrystallized from n-hexane to give 209 mg (yield: 71.3%) of the desired (3 R, 4 R)-4-acetoxy-3-[(R)-1-[dimethyl-(1,1,2-trimethylpropyl)silyloxy]ethyl]azetidin-2-one as white needle-like crystal. The values of its physical properties are shown below.

$[\alpha]_D^{25} = +41.57°$ C. (c=0.5, CHCl$_3$), mp: 80° to 81° C.;

$^1$H NMR (90 MHz, CDCl$_3$) δ (ppm), 0.08 (6 H, s), 0.75 (6 H, s), 0.83 (6 H, d), 1.20 (3 H, d), 1.50 (1 H, m), 2.00 (3 H, s), 3.10 (1 H, dd), 4.12 (1 H, m), 5.75 (1 H, d), 6.53 (NH).

EXAMPLE 26

[Preparation of 4-acetoxy-3-[1-[dimethyl-(1,2-dimethylpropyl)silyloxy]ethyl]azetidin-2-one]

There was dissolved 154 mg of 3-[1-[dimethyl-(1,2-dimethylpropyl)silyloxy]ethyl]-4-trimethylsilyloxyazetidin-2-one in 0.75 ml of pyridine and the solution was cooled to 9° C., to which 0.25 ml of acetic anhydride and 18 mg of p-toluenesulfonic acid.H$_2$O were added and the mixture was stirred at 9° C. for 40 hours. After completion of the reaction, the reaction mixture was treated in the same manner as in Example 2 to give 120 mg of oil. The obtained oil was treated by means of silica-gel column chromatography [n-hexane/ethyl acetate=10/1 (v/v)], and 100 mg (yield: 71.4%) of 4-acetoxy-3-[1-[dimethyl-(1,2-dimethylpropyl)silyloxy]ethyl]azetidin-2-one was obtained as white solid. The values of its physical properties are shown below.

$^1$H NMR (90 MHz, CDCl$_3$) δ (ppm), 0.08 (6 H, s), 0.70 (1 H, m), 0.85 (9 H, d, d, d), 1.20 (3 H, d), 1.80 (1 H, m), 2.02 (3 H, s), 3.10 (1 H, dd), 4.15 (1 H, m), 5.80 (1 H, d), 7.20 (NH).

EXAMPLE 27

[Preparation of (3 R, 4 R)-4-acetoxy-3-[(R)-1-isopropyldimethylsilyoxyethyl]azetidin-2-one]

There was dissolved 304 mg of (3 R, 4 R)-3-[(R)-1-isopropyldimethylsilyloxyethyl]-4-trimethylsilyloxyazetidin-2-one in 1.60 ml of pyridine and the solution was cooled to 9° C., to which 0.53 ml of acetic anhydride and 38 mg of p-toluenesulfonic acid.H$_2$O were added, and the mixture was stirred at 9° C. for 40 hours. After completion of the reaction, the reaction mixture was treated in the same manner as in Example 2 to give 210 mg of oil. The obtained oil was treated by means of silica-gel column chromatography [n-hexane/ethyl acetate =10/1 (v/v)] and further recrystallized from n-hexane, and 164 mg (yield: 59.9%) of the desired (3 R, 4 R)-4-acetoxy-3-[(R)-1-isopropyldimethylsilyloxyethyl]azetidin-2-one was obtained as white crystal. The values of its physical properties are shown below.

$[\alpha]_D^{25} = +54.6°$ (c=0.5, CHCl$_3$), mp: 92° to 94° C.;

$^1$H NMR (90 MHz, CDCl$_3$) δ (ppm), 0.08 (6 H, s), 1.75 (1 H, m), 1.98 (6 H, d), 1.29 (3 H, d), 2.12 (3 H, s), 3.20 (1 H, dd), 4.23 (1 H, m), 5.86 (1 H, d), 6.50 (NH).

EXAMPLE 28

[Preparation of (3 R, 4 R)-4-acetoxy-3-[(R)-1-tert-butyldimethylsilyloxyethyl]azetidin-2-one]

There was dissolved 1.514 g of (3 R, 4 R)-3-[(R)-tert-butyldimethylsilyloxyethyl]-4-trimethylsilyloxyazetidin-2-one [mp: 95° to 96° C., $[\alpha]_D^{25} = -9.5°$ (c=1.0, CHCl$_3$)] in 7.6 ml of pyridine, to which 2.5 ml of acetic anhydride and 0.12 ml of trimethylchlorosilane were added, and the mixture was stirred at 9° C. for 41 hours. The reaction mixture was poured into 150 ml of water and extracted with 150 ml of n-hexane. The organic layer was washed with 5% aqueous solution of NaHCO₃ and further saturated solution of salt, and dried with anhydrous magnesium sulfate. After filtration, the solvent was distilled away under reduced pressure to give 1.250 g of white solid.

From the obtained white solid, 1.000 g of the solid was taken and dissolved in n-hexane. After insoluble substances were filtered off, the resultant was allowed to stand while cooling at −15° C. to give 690 mg (yield: 62.9%) of needle-like crystal. The obtained crystal was found to be the desired (3 R, 4 R)-4-acetoxy-3-[(R)-1-tert-butyldimethylsilyloxyethyl]azetidin-2-one from the following values of its physical properties.

[α]$_D^{25}$ = +50° (c=0.5, CHCl₃), mp: 107° C.;
¹H NMR (90 MHz, CDCl₃) δ (ppm), 0.08 (6 H, s), 0.84 (9 H, s), 1.20 (3 H, d), 2.01 (3 H, s), 3.04 (1 H, dd), 4.12 (1 H, m), 5.76 (1 H, d), 6.73 (NH).

Also, a part of the above white solid was analyzed by means of high performance liquid chromatography [column: YMC-packed column A-303 (ODS), 4.6×250 mm; column temperature: 15° C., solvent: acetonitrile/water=6/4 (v/v), flow rate: 1.1 ml/min., detection: 210 nm], and 1.014 g (yield:74%) of (3 R, 4 R)-4-acetoxy-3-[(R)-1-tert-butyldimethylsilyloxyethyl]azetidin-2-one was found in all.

EXAMPLE 29

[Preparation of (3 R, 4 R)-4-acetoxy-3-[(R)-1-tert-butyldimethylsilyloxyethyl]azetidin-2-one]

There was dissolved 302 mg of (3 R, 4 R)-3-[(R)-1-tert-butyldimethylsilyloxyethyl]-4-trimethylsilyloxyazetidin-2-one in 0.74 ml of methylene chloride, to which 0.77 ml of pyridine and 0.27 ml of acetic anhydride were added. Then, 0.012 ml of trimethylchlorosilane was added thereto under nitrogen atmosphere and the mixture was stirred for 17 hours at room temperature. After the reaction mixture was poured into 30 ml of water and extracted with 30 ml of n-hexane, the organic layer was washed with 5% aqueous solution of NaHCO₃ and saturated solution of salt, and dried with magnesium sulfuric anhydride. The resultant was filtered and the solvent was distilled away under reduced pressure to give 262 mg of white solid. The obtained solid was analyzed by means of high performance liquid chromatography, and 98 mg (yield: 36%) of (3 R, 4 R)-4-acetoxy-3-[(R)-1-tert-butyldimethylsilyloxyethyl]azetidin-2-one was found.

The results of specific rotation, melting point and NMR spectrum of the obtained compound were the same as those in Example 28.

EXAMPLES 30 TO 35 AND COMPARATIVE EXAMPLE 2

[Preparation of (3 R, 4 R)-4-acetoxy-3-[(R)-1-tert-butyldimethylsilyloxyethyl]azetidin-2-one]

The procedure of Example 28 was repeated to prepare (3 R, 4 R)-4-acetoxy-3-[(R)-1-tert-butyldimethylsilyloxyethyl]azetidin-2-one [(II′) shown below] except that various compound (VI) shown in Table 5 was employed as a catalyst and that acetic anhydride was used in an amount of 5.6 moles and pyridine was used in an amount of 19.7 moles to one mole of the (3 R, 4 R)-3-[(R)-tert-butyldimethylsilyloxy-ethyl]azetidin-2-one[(I′) shown below] and the reaction temperature and time were as shown in Table 5. Also, the same preparation as above was carried out without adding the compound (VI), for comparison. The results are shown in Table 5.

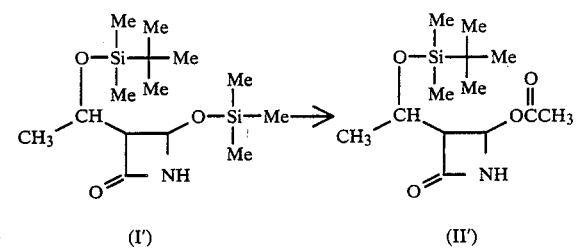

(I′)    (II′)

The results of specific rotation, melting point and NMR of the obtained compound in each Example 30 to 35 were the same as those in Example 28.

TABLE 5

| Ex. No. | Compound (VI) | Amount of the compound (VI) (mole to one mole of the compound (I′)) | Temperature (°C.) | Time (hours) | Yield of the compound (II′) (%) |
|---|---|---|---|---|---|
| 30 | Trimethyliodosilane | 0.2 | 9 | 40 | 73 |
| 31 | Trimethylsilyltrifluoromethanesulfonate | 0.2 | 9 | 40 | 71 |
| 32 | Tert-butylphenylmethylchlorosilane | 0.2 | 9 | 41 | 65 |
| 33 | Tert-butyldimethylchlorosilane | 0.2 | 9 | 41 | 65 |
| 34 | Dimethyldichlorosilane | 0.2 | 9 | 41 | 63 |
| 35 | Tetrachlorosilane | 0.2 | Room temperature | 41 | 52 |
| Com. Ex. 2 | — | 0 | Room temperature | 25 | 10 |

EXAMPLES 36 TO 38

[Preparation of (3 R, 4 R)-4-acetoxy-3-[(R)-1-tert-butyldimethylsilyloxyethyl]azetidin-2-one]

The procedure of Example 28 was repeated to prepare (3 R, 4 R)-4-acetoxy-3-[(R)-1-tert-butyldimethylsilyloxyethyl]azetidin-2-one [(II′) shown below]except that various bases shown in Table 6 were employed and that acetic anhydride was used in an amount of 5.6 moles and trimethylchlorosilane was used in an amount of 0.2 mole to one mole of (3 R, 4 R)-3-[(R)-tert-butyldimethylsilyloxyethyl]-4-trimethyl-silyloxyazetidin-2-one [(I′) shown below] and the reaction temperature and time were as shown in Table 6. The results are shown in Table 6.

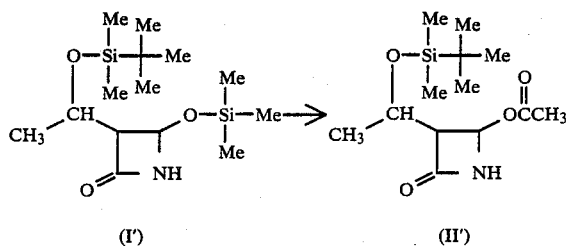

(I')  (II')

The results of specific rotation, melting point and NMR spectrum in each Examples 36 to 38 were the same as those in Example 28.

TABLE 6

| Ex. No. | Base | Amount of base (moles to one mole of the compound (I')) | Temperature (°C.) | Time (hours) | Yield of the compound (II') (%) |
|---|---|---|---|---|---|
| 36 | 3-Picoline | 19.7 | 9 | 62 | 74 |
| 37 | 4-Picoline | 19.7 | 9 | 62 | 61 |
| 38 | 3,4-Lutidine | 19.7 | 9 | 62 | 61 |

EXAMPLE 39

[Preparation of (3 R, 4 R)-4-acetoxy-3-[(R)-1-[dimethyl-(1,1,2-trimethylpropyl)silyloxy]ethyl]azetidin-2-one]

There was dissolved 520 mg of (3 R, 4 R)-3-[(R)-1-[dimethyl-(1,1,2-trimethylpropyl)silyloxy]ethyl]-4-trimethylsilyloxyazetidin-2-one in 2.44 ml of pyridine and the solution was cooled to 9° C. under nitrogen atmosphere, to which 0.81 ml of acetic anhydride and 0.039 ml of trimethylchlorosilane were added, and the mixture was stirred at 9° C. for 40 hours. After completion of the reaction, the reaction mixture was treated in the same manner as in Example 28 to give 401 mg of semi-solid. The obtained semi-solid was treated by means of silica-gel column chromatography [n-hexane/ethyl acetate=10/1 (v/v)] and 338 mg (yield: 71.2%) of the desired (3 R, 4 R)-4-acetoxy-3-[(R)-1-[dimethyl-(1,1,2-trimethylpropyl)silyloxy]ethyl]azetidin-2-one was obtained as white needle-like crystal.

The results of specific rotation, melting point and NMR spectrum of the obtained compound were the same as those in Example 25.

EXAMPLE 40

[Preparation of (3 R, 4 R)-4-acetoxy-3-[(R)-1-isopropyldimethylsilyloxyethyl-]azetidin-2-one]

There was dissolved 301 mg of (3 R, 4 R)-3-[(R)-1-isopropyldimethylsilyloxyethyl]-4-trimethylsilyloxyazetidin-2-one in 1.58 ml of pyridine and the solution was cooled to 9° C. under nitrogen atmosphere, to which were added 0.52 ml of acetic anhydride and 0.025 ml of trimethylchlorosilane, and the mixture was stirred at 9° C. for 40 hours. After completion of the reaction, the reaction mixture was treated in the same manner as in Example 28 to give 229 mg of semi-solid. The obtained semi-solid was treated by means of silica-gel column chromatography [n-hexane/ethyl acetate=10/1 (v/v)] and 176 mg (yield: 64.4%) of the desired (3 R, 4 R)-4-acetoxy-3-[(R)-1-isopropyldimethyloxyethyl]azetidin-2-one was was obtained as white crystal.

The results of specific rotation, melting point and NMR spectrum of the obtained compound were the same as those in Example 27.

EXAMPLE 41

[Preparation of 4-acetoxy-3-[1-[dimethyl-(1,2-dimethylpropyl)silyloxy]ethyl]azetidin-2-one]

There was dissolved 300 mg of 3-[1-[dimethyl-(1,2-dimethylpropyl)silyloxy]ethyl]-4-trimethylsilyloxyazetidin-2-one in 1.47 ml of pyridine and the solution was cooled at 9° C. under nitrogen atmosphere, to which were added 0.49 ml of acetic anhydride and 0.023 ml of trimethylchlorosilane, and the mixture was stirred at 9° C. for 40 hours. After completion of the reactor, the reaction mixture was treated in the same manner as in Example 28 to give 201 mg of semi-solid. The obtained semi-solid was treated by means of silica-gel column chromatography [n-hexane/ethyl acetate=10/1 (v/v)], and 175 mg (yield: 64.2%) of the desired 4-acetoxy-3-[1-[dimethyl-(1,2-dimethylpropyl)-silyloxy]ethyl]azetidin-2-one was obtained as white solid. The values of its physical properties are shown below.

$^1$H NMR (90 MHz, CDCl$_3$) δ (ppm), 0.08 (6 H, s), 0.70 (1 H, m), 0.85 (9 H, d, d, d), 1.20 (3 H, d), 1.80 (1 H, m), 2.02 (3 H, s), 3.10 (1 H, dd), 4.15 (1 H, m), 5.80 (1 H, d), 7.20 (NH).

In addition to the ingredients used in the Examples, other ingredients can be used in the Examples as set forth in the specification to obtain substantially the same result.

What we claim is:

1. A process for preparing a 4-acetoxy-3-hydroxyethylazetidin-2-one derivative having the formula (II):

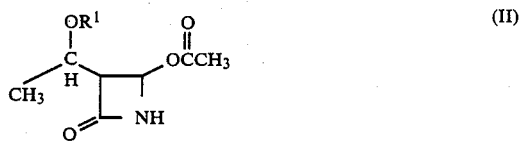

wherein $R^1$ is a protective group for the hydroxyl group, which comprises reacting a β-lactam compound having the formula (I):

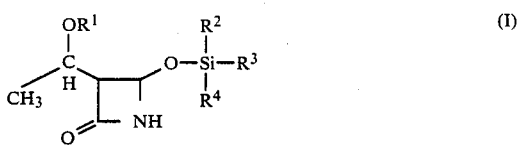

wherein $R^1$ is as defined above and $R^2$, $R^3$ and $R^4$ are the same or different and each is a lower alkyl group having 1 to 4 carbon atoms or an aralkyl group, with acetic anhydride in the presence of a base and a catalyst selected from the group consisting of an organic strong acid, a mineral acid, a Lewis acid, a halogenated acyl compound having the formula (IV):

$$R^8-CO-X \quad (IV)$$

wherein $R^8$ is an alkyl group, an aralkyl group or phenyl group and X is a halogen atom, a halogenated sulfonyl compound having the formula (V):

$$R^9-SO_2-X \quad (V)$$

wherein $R^9$ is an alkyl group, an aralkyl group or phenyl group and X is a halogen atom, and a compound having the formula (VI):

$$(R^{10})_{4-n}-Si(X')_n \quad (VI)$$

wherein $R^{10}$ is a lower alkyl group having 1 to 6 carbon atoms or phenyl group, X' is a halogen atom or $CF_3SO_2O$ group and n is an integer of 1 to 4.

2. The process of claim 1, wherein $R^1$ is a group of the formula (III):

$$\begin{array}{c} R^5 \\ | \\ Si-R^6 \\ | \\ R^7 \end{array} \quad (III)$$

wherein $R^5$, $R^6$ and $R^7$ are the same or different and each is a lower alkyl group having 1 to 6 carbon atoms, provided that $R^1$ may not be trimethylsilyl.

3. The process of claim 1, wherein $R^1$ is tert-butyldimethylsilyl group.

4. The process of claim 1, wherein $R^1$ is isopropyldimethylsilyl group.

5. The process of claim 1, wherein $R^1$ is dimethyl-(1,1,2-trimethylpropyl)silyl group.

6. The process of claim 1, wherein $R^1$ is dimethyl-(1,2-dimethylpropyl)silyl group.

7. The process of claim 1, wherein $R^2$, $R^3$ and $R^4$ are the same and each is methyl group.

8. The process of claim 1, wherein said organic strong acid is an organic sulfonic acid.

9. The process of claim 8, wherein said organic sulfonic acid is p-toluenesulfonic acid or trifluoromethanesulfonic acid.

10. The process of claim 1, wherein said organic strong acid is trifluoroacetic acid.

11. The process of claim 1, wherein said organic strong acid is trichloroacetic acid.

12. The process of claim 1, wherein said mineral acid is hydrogen chloride or phosphoric acid.

13. The process of claim 1, wherein said Lewis acid is boron trifluoride or boron trichloride.

14. The process of claim 1, wherein said halogenated acyl compound is acetyl chloride.

15. The process of claim 1, wherein said halogenated sulfonyl compound is p-toluenesulfonyl chloride.

16. The process of claim 1, wherein said compound having the formula (VI) is trimethylchlorosilane.

17. The process of claim 1, wherein said compound having the formula (VI) is trimethyliodosilane.

18. The process of claim 1, wherein said compound having the formula (VI) is trimethylsilyltrifluoromethanesulfonate.

19. The process of claim 1, wherein said base is pyridine.

20. The process of claim 1, wherein said base is picoline.

* * * * *